(12) United States Patent
Theoharides

(10) Patent No.: US 9,050,275 B2
(45) Date of Patent: Jun. 9, 2015

(54) METHODS OF SCREENING FOR AND TREATING AUTISM SPECTRUM DISORDERS AND COMPOSITIONS FOR SAME

(75) Inventor: Theoharis C. Theoharides, Brookline, MA (US)

(73) Assignee: Theta Biomedical Consulting & Development Co., Inc., Brookline, MA (US)

( * ) Notice: Subject to any disclaimer, the term of this patent is extended or adjusted under 35 U.S.C. 154(b) by 106 days.

(21) Appl. No.: 13/009,282

(22) Filed: Jan. 19, 2011

(65) Prior Publication Data

US 2011/0183019 A1 Jul. 28, 2011

Related U.S. Application Data

(63) Continuation-in-part of application No. 12/534,571, filed on Aug. 3, 2009.

(51) Int. Cl.

| A61K 31/00 | (2006.01) |
|---|---|
| A61K 31/352 | (2006.01) |
| A61K 31/451 | (2006.01) |
| A61K 31/4545 | (2006.01) |
| A61K 31/495 | (2006.01) |
| A61K 31/519 | (2006.01) |
| A61K 31/55 | (2006.01) |
| A61K 33/24 | (2006.01) |
| A61K 36/63 | (2006.01) |
| A61K 45/06 | (2006.01) |
| G01N 33/68 | (2006.01) |

(52) U.S. Cl.
CPC ....... *A61K 31/00* (2013.01); *Y10T 436/143333* (2015.01); *Y10T 436/201666* (2015.01); *A61K 31/352* (2013.01); *A61K 31/451* (2013.01); *A61K 31/4545* (2013.01); *A61K 31/495* (2013.01); *A61K 31/519* (2013.01); *A61K 31/55* (2013.01); *A61K 33/24* (2013.01); *A61K 36/63* (2013.01); *A61K 45/06* (2013.01); *G01N 33/6896* (2013.01); *G01N 2333/54* (2013.01); *G01N 2333/70503* (2013.01); *G01N 2800/28* (2013.01)

(58) Field of Classification Search
None
See application file for complete search history.

(56) References Cited

U.S. PATENT DOCUMENTS

| 5,223,257 A | 6/1993 | Arora |
|---|---|---|
| 5,250,529 A | 10/1993 | Theoharides |
| 5,260,335 A | 11/1993 | Wagner et al. |
| 5,648,355 A | 7/1997 | Theoharides |
| 5,795,905 A | 8/1998 | McCarthy et al. |
| 5,804,594 A | 9/1998 | Murad |
| 5,821,259 A | 10/1998 | Theoharides |
| 5,855,884 A | 1/1999 | Theoharides |
| 5,876,744 A | 3/1999 | Della Valle et al. |
| 5,972,999 A | 10/1999 | Murad |
| 5,980,865 A | 11/1999 | Ahmed |
| 5,994,357 A | 11/1999 | Theoharides |
| 6,020,305 A | 2/2000 | Theoharides |
| 6,136,795 A | 10/2000 | Florio |
| 6,162,787 A | 12/2000 | Sorgente et al. |
| 6,211,195 B1 | 4/2001 | Webb et al. |
| 6,586,448 B1 | 7/2003 | DeNinno et al. |
| 6,689,748 B1 | 2/2004 | Theoharides |
| 6,765,008 B1 | 7/2004 | Chen |
| 6,984,667 B2 | 1/2006 | Theoharides |
| 7,115,278 B2 | 10/2006 | Theoharides |
| 7,799,354 B2 * | 9/2010 | Murdock et al. |
| 2001/0000340 A1 | 4/2001 | Chen et al. |
| 2002/0146393 A1 | 10/2002 | Bell et al. |
| 2003/0194719 A1 | 10/2003 | Waring et al. |
| 2004/0123829 A1 * | 7/2004 | Harima et al. |
| 2004/0213829 A1 * | 10/2004 | Coleman et al. |
| 2005/0220909 A1 | 10/2005 | Theoharides |
| 2006/0013905 A1 | 1/2006 | Tehoharides |
| 2006/0179492 A1 | 8/2006 | Feifel |
| 2006/0210551 A1 | 9/2006 | Lindsberg et al. |
| 2007/0077317 A1 * | 4/2007 | Theoharides |
| 2007/0141187 A1 | 6/2007 | Theoharides |
| 2009/0156668 A1 | 6/2009 | Vitolo et al. |

FOREIGN PATENT DOCUMENTS

| EP | 0426479 | 5/1991 |
|---|---|---|
| GB | 2105193 | 3/1983 |
| IT | 1290440 | 9/1998 |
| WO | WO-98/33494 | 8/1998 |
| WO | WO-00/78320 | 12/2000 |
| WO | WO 2008011364 * | 1/2008 |
| WO | WO 2008011364 A2 * | 1/2008 |

OTHER PUBLICATIONS

Sharma, V et al. Brain Research (2007); 73: 55-63. Modulation of interleukin 1-1β mediated inflammatory response in human astrocytes by flavonoids: Implications in neuroprotection.*
Kumar, A et al. J of Medicinal Food (2008); 11(3): 469-473. Quercetin protects against acute immobilization stress-induced behaviors and biochemical alterations in mice.*
Chauhan, A et al. Pathophysiology (2006); 13: 171-181. Oxidative stress in autism.*
Akhondzadeh, S et al. Journal of Clinical Pharmacy and Therapeutics (2004) 29, 145-150.Cyproheptadine in the treatment of autistic disorder: a double-blind placebo-controlled trial.*
Acta clinica Belgica, 46, 226-232 (1991).
Anesthesia Progress, vol. 30(6): 199-200 (1983).

(Continued)

*Primary Examiner* — Michele Flood
(74) *Attorney, Agent, or Firm* — Wilmer Cutler Pickering Hale and Dorr LLP

(57) ABSTRACT

Disclosed are methods of screening for an autism spectrum disorder, compositions that inhibit the release of molecules that disrupt the blood-brain barrier, compositions for treating autism spectrum disorders, and methods of treating autism spectrum disorders.

11 Claims, 14 Drawing Sheets

(56) References Cited

OTHER PUBLICATIONS

Boushey, R. et al., "Adrenal Cortical Carcinoma," Curr. Treatment Op. Oncol., 2: 355-364 (2001).
Cefali, E.A. et al., "Aspirin reduces cutaneous flushing after administration of an optimized extended-release niacin formulations," Int. J. Clin. Pharm. Ther., vol. 45: 78-88 (2007).
Chines, A. et al., "Systemic Mastocytosis Presenting as Osteoporosis: A Clinical and Histomorphometric Study," J. Clin. Endocrinol. and Metab., vol. 72(1): 140-144 (1991).
Database WPI: 2001-358435—XP002221703, "Compositions comprising hyaluronic acid and flavonoids," (2 pages).
Dermatologic Clinics, vol. 14(3): 447-55 (Jul. 1996).
Devlin, Thomas (ed): Textbook of Biochemistry with Clinical Correlations, 2nd Edition: Ch. 8.5-8.6, 345-351 (1982).
Dimitriadou, V. et al., Histochemical and Ultrastructural Characteristics of Rat Brain Perivascular Mast Cells Stimulated With Compound 48/80 and Carbachol, Neuroscience, vol. 39(1): 209-224 (1990).
Dunn, R.T. et al., "Low-Dose Aspirin and Ibuprofen Reduce The Cutaneous Reactions Following Niacin Administration," Am. J. Thera., 2: 478-480 (1995).
Dvorak, A.M. et al., "Human Gut Mucosal Mast Cell: Ultrastructural Observations and Anatomic Variation In Mast Cell-Nerve Associations in vivo," vol. 98: 158-168 (1992).
Gupta, E. et al., "Lovastatin and Extended-Release Niacin Combination Product: The First Drug Combination for the Management of Hyperlipidemia," Heart Disease, vol. 4: 124-137 (2002).
Gupta, E. et al., "Lovastatin and Extended-Release Niacin Combination Product: The First Drug Combination for the Management of Hyperlipidia," Heart Disease, vol. 4, 124-137 (2002).
Hendriks, J. et al., "Flavonoids Influence Monocytic CTPase Activity and Are Protective In Experimental Allergic Encephalitis," J. Exp. Med., vol. 200(12): 1667-1672 (2004).
Hendriks, J. et al., "Flavonoids Influence Monocytic GTPase Activity and Are Protective in Experimental Allergic Encephalitis," J. Exp. Med., vol. 200(12): 1667-1672 (Dec. 20, 2004).
International Search Report and Written Opinion, International Patent Application No. PCT/US08/86059, mailed Jan. 26, 2009 (7 pages).
International Search Report issued for PCT/US02/00476, dated Dec. 16, 2002 (6 pages).
International Search report issued for PCT/US09/52577, mailed on Nov. 24, 2009 (5 pages).
International Search Report issued for PCT/US95/01392, dated May 31, 1995 (4 pages).
Irani, A-M, et al., "Mast Cell Changes in Scleroderma," Arth. and Rheuma., vol. 35(8): 933-939 (Aug. 1992).
Kimata, M. et al., "Effects of luteolin, quercetin and baicalein on immunoglobulin E-mediated mediator release from human cultured mast cells," Clin. and Exper. Allergy, vol. 30, 501-508 (2000).
Koblenzer, C.S. "Neurotic excoriations and dermatitis artefacta," Dermatologic Clinics, vol. 14(3): 447-455 (Jul. 1996).
Lambracht-Hall, M. et al., "Serotonin Release From Rat Brain Mast Cells," Neuroscience, vol. 39(1) 199-207 (1990).
Letters to the Editor, J. Allergy Clin. Immunol., vol. 119(2): 498-499 (Oct. 18, 2006).
Lidor, C. et al., "Osteoporosis as the Sole Presentation of Bone Marrow Mastocytosis," J. Bone Min Res., vol. 5(8): 871-876 (1990).
Mathias, J. et al., "Debilitating 'Functional' Bowel Disease Controlled by Leuprolide Acetate, Gonadotropin-Releasing Hormone (GnRH) Analog," Digestive Diseases and Sciences, vol. 34(5): 761-766 (May 1989).
Matsuda, K. et al., "Inhibitory Effects of Sialic-Acid- or N-Acetylglucosamine-Specific Lectins on Histamine Release Induced by Compound 48/80, Bradykinin and a Polyethylenimine in Rat Peritoneal Mast Cells," Jpn. J. Pharmacol., 64: 1-8 (1994).
Mezzapesa, D. et al., "Glatiramer acetate in multiple sclerosis," Expert Rev. Neurotherapeutics (5)4: 451-458 (2005).
Mezzapesa, D.M. et al., "Glatiramer acetate in multiple sclerosis," Expert Rev. Neurotherapeutics 5(4): 451-458 (2005).
Morrow, J. et al., "Identification of Skin as a Major Site of Prostaglandin D2 Release Following Oral Administration of Niacin in Human," J. Invest. Derm., vol. 98(5): 812-815 (1992).
Morrow, J.D., et al., "Release of markedly increased quantities of prostaglandin D2 in vivo in humans following the administration of nicotinic acid," Prostaglandins, vol. 38(2): 263-274 (1989).
Owens, M.J. and Nemeroff, C.B., "Physiology and Pharmacology of Corticotropin-releasing Factor," Pharmacological Reviews, vol. 43(4): 425-615 (1991).
Parodi et al., "Terfenadine Prophylaxis in Migraine," Arch. Psicol. Neurol. Psichiatr. vol. 49(3): 299-303 (1988).
Pearce, F.L. "Mast cell heterogeneity," TIPS: 165-167 (Apr. 1983).
Prior, A. and Read, N.W. "Reduction of rectal sensitivity and post-prandial motility by granisetron, a 5HT3 receptor antagonist, in patients with irritable bowel syndrome (IBS)," Brit. Soc. of Gasteroent., A1174 (1 page).
Read, N.W. "Irritable bowel syndrome (IBS)—definition and pathophysiology,", vol. 130: 7-13 (1987).
Rockoff, S.D. and Armstrong, J.D. "Parathyroid Hormone as a Stimulus to Mast Cell Accumulation In Bone," Calc. Tiss. Res., 5: 49-55 (1970).
Russell, A.L. and McCarty, M.F. "Glucosamine for migraine prophylaxis?" Medical Hypotheses, 55(3): 195-198 (2000).
Seibold, J. et al., "Dermal Mast Cell Degranulation in Systemic Sclerosis," Arth. and Rheuma., vol. 33(11): 1702-1709 (Nov. 1990).
Shapiro, G. et al., "Cromolyn Sodium: A Review," Pharmacotherapy, vol. 5(3): 156-170 (May/Jun. 1985).
Shoskes, D., et al., "Quercetin in men with category III chronic prostatis: a preliminary prospective, double-blind, placebo-controlled trial," Urology, 54(6): 960-963 (1999).
Simopoulos, A.P., Visioli F. (eds): Mediterranean Diets. World Rev. Nutr. Diet. Basel, Karger, vol. 87: 56-77 (2000).
Singleton, V.L. and Rossi, J.A. "Colorimetry of Total Phenolics with Phosphomolybdic-Phosphotungstic Acid Reagents," Phenolics Determination, pp. 144-158.
Singleton, V.L. and Rossi, Jr., Joseph, "Colorimetry and Total Phenolics With Phosphomolybdic-Phosphotungstic Acid Reagents," Phenolics Determination, pp. 144-158.
Split et al., "Ketotifen in the treatment of Chronic ClusterHeadache," Headache, vol. 24(30: 147-148: 1984).
Split et al., Neurol. Neurochir. Pol., vol. 18(2): 105-109 (1984).
Stefanini, G.F. et al., "Oral disodium cromoglycate treatment on irritable bowel syndrome: An open study on 101 subjects with diarrheic type," vol. 87: 55-57 (1992).
Sundaram, K. et al., "Antagonists of luteinizing hormone releasing hormone bind to rat mast cells and induce histamine release," Agents and Actions, vol. 25(3/4): 307-313 (1988).
Tauberg, J. et al., "Stress-induced urticaria associated with local anesthetic administration," Anesthesia Progress, vol. 30(6): 199-200 (1983).
Theoharides, T. "Mast Cells and Migraines," Brief Proposal, 4 pages (1983).
Theoharides, T. et al., "Bladder Mast Cell Activation in Interstitial Cystitis," Seminars of Urology, vol. IX(2): 74-87 (May 1991).
Theoharides, T.C. "Mast Cells: The Immune Gate To The Brain," Life Sciences, vol. 46: 607-617 (1990).
Theoharides, T.C. and Douglas, W.W. "Somatostatin Induces Histamine Secretion From Rat Peritoneal Mast Cells," Endocrinology, vol. 102(5): 1637-1640) (Nov. 7, 1977).
Theoharides, T.C., "Histamine2 (H2)-Receptor Antagonists in the Treatment of Urticaria," Drugs 37: 345-355 (1989).
Theoharides, T.C., "The Mast Cell: A Neuroimmunoendocrine Master Player," Int. J. Tiss. Reac. XVIII(1), 1-21 (1996).
Trichopoulou, A. et al., "Cancer and Meditarranean Dietary Traditions," Cancer Epidemiology, Biomarkers, & Prevention, vol. 9: 869-873 (Sep. 2000).
Trichopoulou, A. et al., "Diet and Survival of Elderly Greeks: a link to the past1-4." Am. J. Clin. Nutri., vol. 61(suppl.): 1346S-50S (1995).
Tsakalos, N, et al., "Induction of Mast Cell Secretion by Parathormone," vol. 32(2): 355-360 (1983).

(56) References Cited

OTHER PUBLICATIONS

Unlisted Drugs, vol. 20(11): 167 (Nov. 1968).
Urade, Y. et al., "The Major Source of Endogenous Prostaglandin D2 Production is Likely Antigen-Presenting Cells," J. Immunol., 143(9): 2982-2989 (Nov. 1, 1989).
Verbeek, R. et al., "Oral flavonoids delay recoverly from experimental autoimmune encephalomyelitis in SJL mice," Biochem. Pharm., 70: 220-228 (2005).
Wesolowski, Autism: Unknown Causes, Known Effects, J. for Pre-Health Affiliated Students, vol. V(1): 19-20 (Winter 2005).
Weston, A. et al., "Terminal Ileal Mucosal Mast Cells In Irritable Bowel Syndrome," Dig. Diseases and Sci., vol. 38(9): 1590-1595 (Sep. 1993).
Weston, AP, et al., "Terminal ileal mucosal mast cells in irritable bowel syndrome." Dig. Dis. Sci., vol. 38(9): 1590-5 (Sep. 1993).
Wing, "Autism Spectrum Disorders" BMJ J. vol. 312: 327-328 (Feb. 10, 1996).
Theoharides, et al, "A Case Series of a Luteolin Formulation (Neuroprotek®) in Children With Autism Spectrum Disorders," Int'l J. Immunopathology and Pharma., vol. 25, No. 2, 317-323 (2012).
Taliou, et. al, "An Open-Label Pilot Study of a Formulation Containing the Anti-Inflammatory Flavonoid Luteolin and Its Effects on Behavior in Children With Autism Spectrum Disorders," Clinical Therapeutics, vol. 35, No. 5, pp. 592-602, 2013.
Yu, et. al, "Mutagenicity of Proanthocyanidins," Food Chem. Toxic., vol. 25, No. 2, pp. 135-139, 1987.

* cited by examiner

Figure 1: Serum levels of neurotensin in autistic patients and normal controls.

Figure 2: Serum levels of IL-6 in autistic patients and normal controls.

US 9,050,275 B2

METHODS OF SCREENING FOR AND TREATING AUTISM SPECTRUM DISORDERS AND COMPOSITIONS FOR SAME

FIELD OF THE INVENTION

This application is a continuation-in-part application of U.S. patent application Ser. No. 12/534,571, filed Aug. 3, 2009. The entire disclosures of that application are relied on herein and incorporated into this application by reference.

FIELD OF THE INVENTION

The present disclosure is in the field of medicine. More specifically, this disclosure relates to methods, certain compositions, and the use of those methods and compositions for screening for and treating autistic spectrum disorders. This disclosure also relates to methods of screening for autism spectrum disorders based on certain biomarkers.

BACKGROUND

Autism spectrum disorders (ASDs) are pervasive neurodevelopmental disorders diagnosed in early childhood when acquired skills are lost or the acquisition of new skills becomes delayed. ASDs onset in early childhood and are associated with varying degrees of dysfunctional communication and social skills, in addition to repetitive and stereotypic behaviors. In many cases (25%-50%), a period of seemingly normal development drastically shifts directions as acquired skills are lost or the acquisition of new skills becomes delayed.

In recent years, the number of people with an ASD has increased considerably to approximately 1 in 150 children, but it is not clear whether this increase is because of a higher prevalence of the disorder, improved awareness by clinicians, or a combination of both.

One proposed cause for the increased number of people with an ASD is an increase in exposure to mercury from environmental and medicinal sources. Mercury exposure causes immune, sensory, neurological, motor, and behavioral dysfunction similar to symptoms associated with autism. Methyl mercury ingestion from fish has been previously linked to neurological damage. Ethyl mercury linked to thiosalicylate, known as thimerosal, has been used extensively as a preservative in vaccines and has been suspected to contribute to the pathogenesis of autism. Mercury chloride ($HgCl_2$) is known to induce the release of bioactive molecules such as histamine and vascular endothelial growth factor (VEGF) that could disrupt the protective blood-brain barrier (BBB).

A number of studies have reported that patients with ASDs have in their blood antibodies against brain proteins. Brain blood vessels can become leaky (permeable) at some point during a child's development and allow circulating immune cells to be exposed to brain proteins that were mistaken by the immune system as foreign. As a result, antibodies are made against those brain proteins. Such antibodies against brain proteins can disrupt normal brain function and, alone or together with other circulating immune cell-derived destructive molecules, can contribute to brain damage and to the pathogenesis of ASDs. Moreover, increased brain blood vessel leakage can increase intracranial pressure and contribute to macrocephaly reported in many children with ASDs, thus further compromising brain function.

There is currently no explanation for what causes the brain blood vessels to become leaky, i.e., what causes the disruption of the blood-brain barrier (BBB). Identification of molecules that can make brain blood vessels leak could lead to the development of diagnostic biomarkers and serve as targets for treating ASDs. Preventing brain blood vessel leakage in susceptible children, or reversing brain blood vessel leakage in children who have already developed ASDs, could provide a novel therapeutic intervention.

Currently, there are no known defined mechanisms of pathogenesis, diagnostic biomarkers, or curative therapy available for ASDs. An important need therefore exists for methods and compositions that are effective to screen for and treat ASDs. Various embodiments of the invention address these needs.

SUMMARY OF THE INVENTION

It has been discovered that measurement of certain serum biomarkers capable of making gut and/or brain blood vessels leaky can diagnose patients with ASDs. It has also been discovered that certain compositions can inhibit, directly or through inhibition of the release of biomarkers that induce, leakage of brain vessels that would otherwise allow entry of noxious molecules in the brain. The compositions disclosed herein have been found to improve the conditions associated with ASDs through inhibition of blood vessel leakage, as determined by behavioral improvement and as noted in the examples disclosed herein. Together, these data support that modulation, and, in particular, inhibition, of brain blood vessel leakage is a valuable intervention point for the treatment of ASDs. This discovery has been exploited to develop the present application, which includes methods and compositions for treating ASDs in a subject, as well as methods for screening for an ASD in a subject suspected of having an ASD.

One aspect of the application is directed to a method of treating an ASD in a subject. In this method, a composition comprising one or more flavonoids with olive kernel extract, alone or in combination with a serotonin blocker, a histamine-1 receptor antagonist, a histamine-3 receptor agonist, an antipsychotic agent, a heavy metal chelator, a neurotensin blocker, a defensin, and a physiologically acceptable carrier, is administered to a subject in need thereof, wherein the composition modulates the leakage of brain blood vessels. In some embodiments, the composition comprises luteolin, quercetin, and rutin with olive kernel extract.

In particular embodiments, the composition inhibits gut and or brain blood vessel leakage.

In certain embodiments, the ASD is autism.

In other embodiments, the ASD is Asperger's syndrome, atypical autism otherwise known as pervasive developmental disorder not otherwise specified (PDD-NOS), Rett syndrome, childhood disintegrative disorder, or sensory integration dysfunction.

In particular embodiments, the flavonoid is apigenin, astragaline, (−)-epigallocatechin-3 gallate, genistein, hesperetin, hesperidin, kaempferol, luteolin, myricetin, quercetin, or rutin.

In yet other embodiments, the serotonin blocker is the serotonin receptor antagonist azatadine or cyproheptadine.

In yet other embodiments, the histamine-1 receptor antagonist is azatadine, azelastine, cyproheptadine, hydroxyzine, merelastine, or rupatadine.

In additional embodiments, the histamine-3 receptor agonist is R(−)-α-methyl histamine, $N^\alpha$-methyl histamine, $N^\tau$-methyl histamine, α-$N^\alpha$-dethylhistamine, α,β-dimethyl histamine, N^α-methyl-α-(dimethyl)histamine, N^α-methyl-α-(chloromethyl)histamine, or α,β-difluoro-N^α-(fluoromethyl)histamine.

In some embodiments, the neurotensin blocker is SR48692, SR142948A (Sanofi-Aventis, Paris, France).

In other embodiments, the antipsychotic agent is risperidone.

In certain embodiments, the heavy metal chelator is meso-2,3-dimercaptosuccinic acid (DMSA).

Another aspect of the application is directed to a method of inhibiting brain blood vessel leakage in a subject. In this method, a composition comprising one or more flavonoids, alone or in combination with, a serotonin blocker, a histamine-1 receptor antagonist, a histamine-3 receptor agonist, an antipsychotic agent, a neurotensin blocker, a defensin, a heavy metal chelator, olive kernel extract and a physiologically acceptable carrier, is administered to a subject in need thereof, wherein the composition modulates the leakage of brain blood vessels.

In particular embodiments, the flavonoid is apigenin, astragaline, (−)-epigallocatechin-3 gallate, genistein, hesperetin, hesperidin, kaempferol, luteolin, myricetin, quercetin, or rutin. In other embodiments, the composition comprises luteolin, quercetin, and rutin with olive kernel extract.

In other embodiments, the serotonin blocker is azatadine or cyproheptadine.

In yet other embodiments, histamine-1 receptor antagonist is azatadine, azelastine, cyproheptadine, hydroxyzine, merelastine, or rupatadine.

In additional embodiments, the histamine-3 receptor agonist is R(−)-α-methyl histamine, N^α-methyl histamine, N^τ-methyl histamine, α-N^α-dethylhistamine, α,β-dimethyl histamine, N^α-methyl-α-(dimethyl)histamine, N^α-methyl-α-(chloromethyl)histamine, or α,β-difluoro-N^α-(fluoromethyl)histamine.

In some embodiments, the neurotensin blocker is SR48692, SR142948A (Sanofi-Aventis, Paris, France).

In other embodiments, the antipsychotic agent is risperidone.

In other embodiments, the heavy metal chelator is meso-2,3-dimercaptosuccinic acid (DMSA).

In other embodiments, the defensin is peptide LL37.

Yet a further aspect of the application is directed to a method of screening a subject to determine whether the subject has an ASD. The method comprises collecting blood serum from a subject suspected of having an ASD. Next, the serum sample is assayed for the level of a certain biomarker or biomarkers. Finally, the level of biomarker or biomarkers is compared against the level of the same biomarker or biomarkers from a control subject known not to have an ASD. A higher level of the biomarker, or a significantly different level of the biomarker, in a subject suspected of having an ASD indicates that the subject may have an ASD. In some embodiments, the levels of two or more biomarkers are measured in the subject. In further embodiments, whether the two or more biomarkers differ significantly, where such significant differences indicate that the subject may possibly have an ASD, is determined by an algorithm.

In some embodiments, the biomarker is genomic DNA, mitochondrial DNA, an anti-mitochondrial DNA antibody, an anti-mitochondrial antibody, interleukin-6 (IL-6), IL-8, IL-9, IL-13, IL-17, IL-33, prostaglandin D2, corticotrophin-releasing hormone, brain-derived neuroptrophic factor, heparin sulfate, neurotensin, thymus stromal lymphopoietin, vascular endothelial growth factor (VEGF), vasoactive intestinal peptide, platelet activating factor (PAF), AMA-M2 antibodies, or tryptase.

In other embodiments, these biomarkers may be expressed at higher levels and produced by peripheral blood lymphocytes with or without stimulation by triggers such as phytohemagglutinin (PHA), or NT, or specific anti-brain antibodies. In yet other embodiments, higher levels of these biomarkers may be identified in the cerebrospinal fluid (CSF).

Another aspect of this disclosure is directed to methods of inhibiting release of molecules that disrupt the blood-brain barrier, comprising administering to the subject an effective amount of one or more of thiosalicylate, alkyl thiosalicylate, luteolin, quercetin, rutin, or 7,8-dixydroxyflavone.

In an additional aspect of the application, a composition for treating an ASD is provided. The composition comprises a unique combination of luteolin, quercetin, and rutin with olive kernel extract, alone or in combination with, a histamine-1 receptor antagonist, a histamine-3 receptor agonist, a serotonin blocker, an antipsychotic agent, a neurotensin blocker, a heavy metal chelator, and a physiologically acceptable carrier. The composition modulates the leakage of brain blood vessels.

Another aspect of the application is directed to a kit to treat a subject with an ASD. The kit comprises at least one dosage of a composition comprising one or more flavonoids, alone or in combination with a histamine-1 receptor antagonist, a histamine-3 receptor agonist, a serotonin blocker, an antipsychotic agent, a neurotensin blocker, a defensin, a heavy metal chelator, olive kernel extract and a physiologically acceptable carrier for administration to the subject.

In some embodiments, the dosage is in a container, which can be sterile, containing an effective dose of the composition and a physiologically acceptable vehicle. The kit can further comprise a label or instructions to treat a subject with an ASD with the composition.

A further aspect of the application is directed to a kit to screen a biological sample for an ASD. The kit comprises of a rapid assay for blood levels of NT, IL-6, IL-9 and mitochondrial DNA or other mitochondrial components.

In some embodiments, the dosage is in a container, which can be sterile and can sample the blood directly from the subject in question by self-administration. The kit can further comprise a label or instructions to screen a biological sample for an ASD with the composition.

DESCRIPTION

Figure 1:
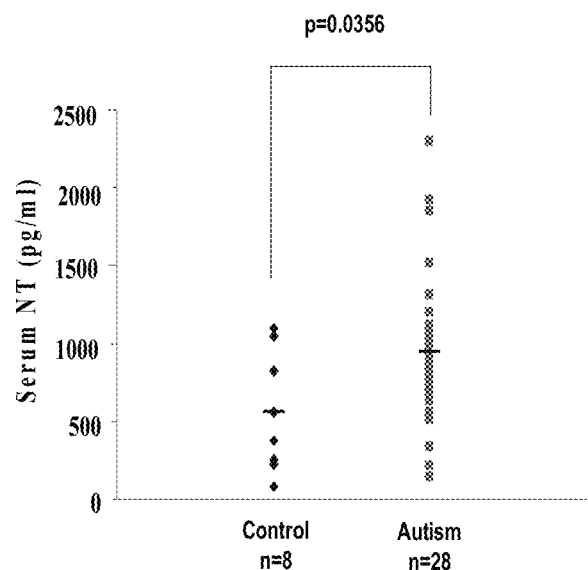
FIG. 1 is a graphic representation of data showing serum levels of neurotensin (NT) of individual patients (2-4 years old with autism) and age-matched normally developing control patients. The data indicate that there is a statistically significant NT increase in children with autism.

This application relates to methods and compositions for inhibiting brain blood vessel leakage, methods and compositions for screening for and treating autism spectrum disorders, methods and compositions for inhibiting mast cell activation, and to pharmaceutical compositions comprising these compositions.

Throughout this application, various patents, patent applications and publications are referenced. The disclosures of these patents, patent applications, and publications in their entireties are incorporated into this application by reference in order to more fully describe the state of the art as known to those skilled therein as of the date of this application. This disclosure will govern in the instance that there is any inconsistency between the patents, patent applications and publications and this disclosure.

DEFINITIONS

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60-20% of 60 and 60+20% of 60 (i.e., between 48% and 72%).

The terms "autism spectrum disorder" and "ASD" or "ASDs" are used in this disclosure to refer to a spectrum of disorders characterized by abnormalities of social interactions and communication, as well as restricted interests and repetitive behavior. This spectrum includes, but is not limited to, autistic disorder, Asperger's syndrome, childhood disintegrative disorder, and atypical autism or pervasive developmental disorder not otherwise specified (PPD-NOS), as well as Rett syndrome and tuberous sclerosis.

The term "carrier" is used in this disclosure to encompass carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "composition" is used in this disclosure to mean a combination or mixture of one or more substances.

The terms "effective amount" and "therapeutically effective amount" are used in this disclosure to refer to an amount of a composition that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The phrase "pharmaceutically acceptable" is used in this disclosure to refer to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "subject" is used in this disclosure to include, without limitation, a human or an animal. Exemplary animals include, but are not limited to, mammals such as mouse, rat, guinea pig, dog, cat, horse, cow, pig, monkey, chimpanzee, baboon, or rhesus monkey.

"Synergistic" is used in this disclosure to mean "coordinated or correlated action by two or more structures or drugs" [*Stedman's Medical Dictionary,* 23rd edition, Williams & Wilkins, Baltimore, 1976].

The term "treating" is used in this disclosure to mean the reduction or amelioration of at least one symptom of any disorder to any extent, and includes, but does not require, a complete cure of the disorder. Treating can be curing, improving, or partially ameliorating a disorder.

"Brain blood vessel leakage" is used in this disclosure to mean leakage from blood vessels, especially as they pertain to the brain, otherwise referred to as increased vascular permeability or blood-brain barrier disruption. The same holds true for gut blood vessels and the gut-blood barrier.

The terms "screen", "screen for", and "diagnose" are used interchangeably in this disclosure.

The term "blocker" is used to mean inhibition, prevention, neutralization, or amelioration of the particular molecules to which it refers. "Blocker" includes, but is not limited to, use of an antagonist, an antibody, a soluble receptor, a receptor variant, or any other inhibitor.

The following abbreviations are used in this disclosure and having the following definitions: Aberrant Behavior Checklist is abbreviated as "ABC"; interleukin is abbreviated "IL" (e.g., interleukin-6 is "IL-6"); neurotensin is abbreviated as "NT"; platelet activating factor is abbreviated as "PAF"; phytohemagglutinin is abbreviated as "HPA"; vascular endothelial growth factor is abbreviated as "VEGF"; minute or minutes is abbreviated "min"; mt is "mitochondrial" and mtDNA is "mitochondrial DNA." Thymus stroma lymphopoietin is abbreviated as "TSLP". Tumor necrosis factor is abbreviated as "TNF"; vascular endothelial growth factor is abbreviated as "VEGF."

Compositions

Aberrant, or immature development, or disruption of the integrity of brain blood vessels exposes the brain to noxious molecules that can adversely affect its function. Such exposure can contribute or lead to the development of ASDs. Blood from children with ASDs often contains a number of autoantibodies against brain peptides indicating that there must have been increased brain blood vessel vascular permeability at some point in order for immune cells to enter the brain and produce antibodies against certain brain proteins.

It has been discovered that a composition comprising one or more flavonoids and olive kernel extract, alone or in combination with a histamine-1 receptor antagonist, a histamine-3 receptor agonist, a serotonin blocker, an antipsychotic agent, a neurotensin blocker, a heavy metal chelator, olive kernel extract and a physiologically acceptable carrier have synergistic effects when used, without or with a conventional clinical treatment, to treat ASDs. The olive kernel extract alone may be used to improve the transmembrane transport of difficult-to-absorb biomolecules in the brain.

In some embodiments, the composition comprises luteolin, quercetin, and rutin with olive kernel extract.

In certain embodiments, the autism spectrum disorder is autism.

In other embodiments, the autism spectrum disorder is Asperger's syndrome, Rett syndrome, childhood disintegrative disorder, or pervasive developmental disorder not otherwise specified (PPD-NOS).

In particular embodiments, the flavonoid is apigenin, astragaline, (−)-epigallocatechin-3 gallate, genistein, hesperetin, hesperidin, kaempferol, luteolin, myricetin, quercetin, or rutin.

In yet other embodiments, histamine-1 receptor antagonist is azatadine, azelastine, cyproheptadine, hydroxyzine, merelastine, or rupatadine.

In additional embodiments, the histamine-3 receptor agonist is R(−)-α-methyl histamine, $N^\alpha$-methyl histamine, $N^\tau$-methyl histamine, α-$N^\alpha$-dethylhistamine, α,β-dimethyl histamine, $N^\alpha$-methyl-α-(dimethyl)histamine, $N^\alpha$-methyl-α-(chloromethyl)histamine, or α,β-difluoro-$N^\alpha$-(fluoromethyl)histamine.

In some embodiments, the serotonin blocker is cyproheptadine.

In some embodiments, the neurotensin blocker is SR48692, SR 142948A (Sanofi-Aventis, Paris, France).

In other embodiments, the antipsychotic agent is risperidone.

In some embodiment, the heavy metal chelator is meso-2,3-dimercaptosuccinic acid (DMSA).

The olive kernel extract component is described in U.S. Publication No. 2006/0013905, which is fully incorporated into this application by reference.

Inhibition of Mast Cell Activation

Mast cells are potential targets for environmental agents with immunotoxic effects because they are mostly located in the skin, respiratory and gastrointestinal tracts. Mast cells are critical for allergic reactions, for innate and acquired immunity, as well as in inflammation. Non-allergic mast cell triggers can derive from either the gut or the brain, and include neuropeptides such as Neurotensin (NT) and Substance P ("SP"). Mercury and $HgCl_2$ also activate human mast cells.

Once activated, mast cells secrete numerous vasoactive, pro-inflammatory and neurotoxic molecules; these include histamine, prostaglandin $D_2$, IL-6, IL-8, IL-9, IL-13, IL-33, tumor necrosis factor (TNF), and VEGF, an isoform of which is vasodilatory and is overexpressed in delayed hypersensitivity reactions. In fact, mast cells can release VEGF, IL-6 and other mediators "selectively" without degranulation, leading to "allergic-like" symptoms not evidenced by typical diagnostic tests. Such mediators could disrupt the blood-brain barrier (BBB), permitting brain inflammation and further increasing brain $HgCl_2$ levels, especially since $HgCl_2$ can cross the BBB through a transport mechanism.

Exposure to mercury, alone or in combination with neuroptides, stress hormones or environmental triggers, at critical developmental periods may contribute to the pathogenesis of neurodevelopmental disorders such as autism, especially in subjects with autism susceptibility genes. Such subjects may be further vulnerable because of mast cell sensitivity or activation by other triggers. For instance, the incidence of autism is tenfold higher in mastocytosis patients (1/10 children), characterized by increased number of hyperactive mast cells in the skin and other tissues, than the general population (1/100 children).

It has been surprisingly discovered that thiosalicylate and alkyl thiosalicylate block mast cell activation. Thus, although mercury activates mast cells, it has been surprisingly discovered that the thiosalicylate part of thimerosal actually reduces the detrimental affect of the mercury in humans because it inhibits mast cell activation. This disclosure provides compositions for the inhibition of mast cell activation comprising thiosalicylate or alkyl thiosalicylate and methods for inhibiting mast cell activation using compounds comprising thiosalicylate or alkyl thiosalicylate. The alkyl group can contain from about 1 to about 8 carbon atoms, sometimes from about 1 to about 6 carbon atoms and includes, but is not limited to, methyl, ethyl, propyl, butyl, pentyl, hexyl, heptyl, and octyl. The alkyl group can be straight-chain or branched.

The methods for inhibiting mast cell activation and inhibiting subsequent brain vessel leakage comprise administering to a patient at least one composition comprising an effective amount of one or more alkyl thiosalicylates, alone or together with luteolin. The patient may have been exposed to mercury, or may be known to be exposed to mercury in the near future, or may not be exposed to mercury at all. The inhibition can be assessed by measuring the levels of certain biomarkers such as the mast cell secreted molecules discussed above, and comparing those levels to the levels of the same certain biomarkers in control subjects, usually of the same sex and age, known not to have an ASD.

This disclosure is also directed to methods of inhibiting mercury-induced and SP-induced mast cell activation. As seen in the examples, the ability of luteolin to inhibit the effect of SP and HgCl2 on VEGF release is impressive. Luteolin can inhibit mast cell activation and mast cell-dependent stimulation of activated T cells. Luteolin is anti-inflammatory, inhibits IL-6 release from microglia, and can inhibit autism-like behavior in mice. Luteolin (5,7,3',4'-tetrahydroxyflavone) is closely related to 7,8-dixydroxyflavone which mimics brain-derived neurotrophic factor (BDNF), which is neuroprotective.

The methods for inhibiting mercury-induced and SP-induced mast cell activation comprise administering to a patient at least one composition comprising an effective amount of luteolin or 7,8-dixydroxyflavone. The patient may have been exposed to mercury, or may be known to be exposed to mercury in the near future, or may not be exposed to mercury at all. The inhibition can be assessed by measuring the levels of certain biomarkers such as the mast cell secreted molecules discussed above, and comparing those levels to the levels of the same certain biomarkers in control subjects, usually of the same sex and age, known not to have an ASD.

Although not intended to be bound by any theory, luteolin, and thiosalicylate may work by preventing intracellular calcium elevations since thimerosal increased cytosolic calcium levels in thymus lymphocytes as $HgCl_2$ did in PCl2 cells. Alternatively, either one or both may act through inhibition of extracellular release of mitochondria.

Mitochondrial DNA

Mitochondria evolved from bacteria in a symbiotic relationship with eukaryotic cells and are typically prevented from being released extracellularly by autophagy. When mitochondrial DNA (mtDNA) is released extracellularly, it results in an autoimmune response by triggering toll-like receptors (TLRs) mimicking the action of bacteria.

It has surprisingly been discovered that mtDNA that is released extracellularly induces an autoimmune response through release of molecules that contribute either to inflammation and/or to the disruption of the gut-blood or blood-brain barriers that contributes to the pathogenesis of autism. Thus, it has been surprisingly discovered that increased levels of mtDNA can serve as a biomarker to screen for an ASD. Furthermore, because mtDNA activates TLRs on immune or glial cells to release pro-inflammatory cytokines, such as IL-6, IL-8, IL-9 or TNF, these increased levels of these cytokines can also serve as biomarkers when screening for an ASD.

Extracellular serum mitochondrial DNA (mtDNA) has not previously been associated with a neuropsychiatric disease. Moreover, anti-mt antibodies have been clinically detected only in primary biliary cirrhosis, which is totally unrelated to ASDs. Extracellular mtDNA release has been reported following TNF treatment of murine embryonic fibroblasts, but this was accompanied by caspase-dependent cell death.

This disclosure provides methods of screening a subject to determine whether the subject has an ASD. The method comprises collecting blood from a subject suspected of having an ASD. Next, the serum or plasma is separated from the sample is assayed for the level of a mtDNA. Finally, the level of the extracellular mtDNA or other mitochondrial components is compared against the level from a subject known not to have an ASD. A higher level of the mtDNA in a subject suspected of having an ASD indicates that the subject may have an ASD.

There is no reason to suspect that mitochondrial components in the examples derive from apoptotic or necrotic cells because no GAPDH genomic DNA was detected indicating there was no nuclear damage.

Figure 8A:
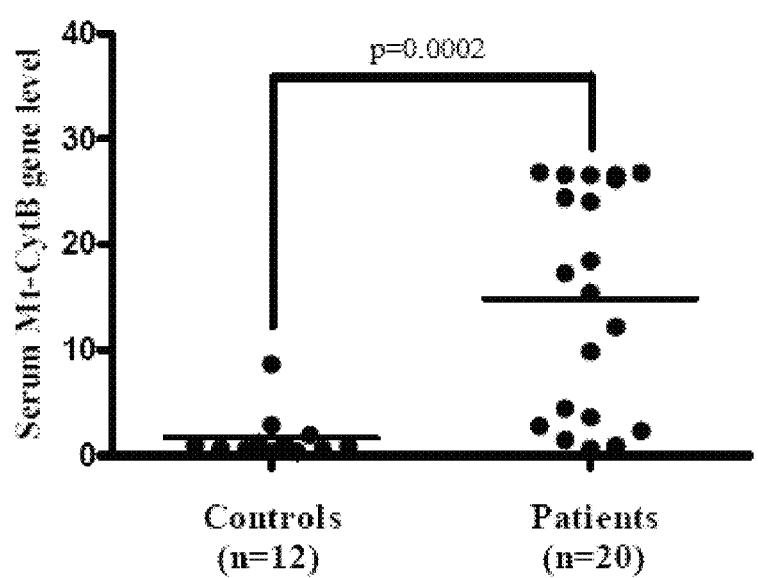
FIGS. 8A and 8B are a graphic representations of data showing that the serum from young autistic children contains significantly higher amounts of mitochondrial cytochrome B (mt-CytB) and for mt-7S.
Figure 8B:
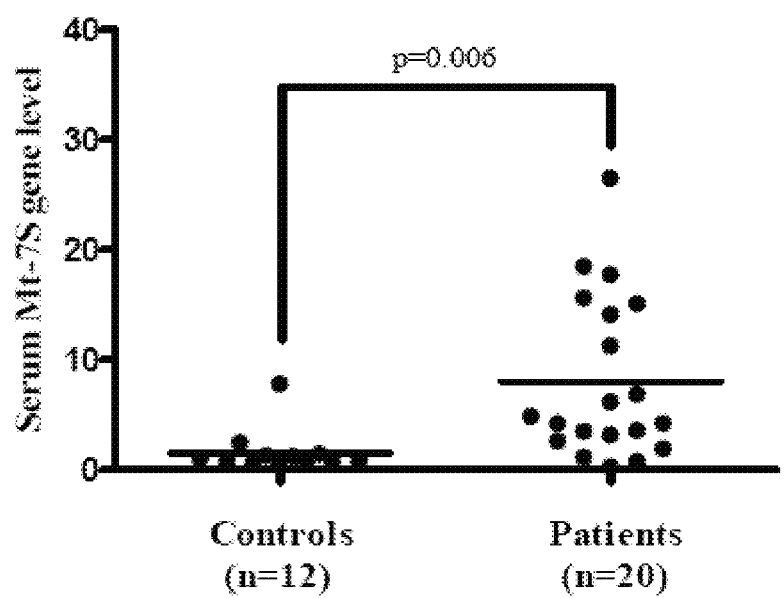
Figure 9:
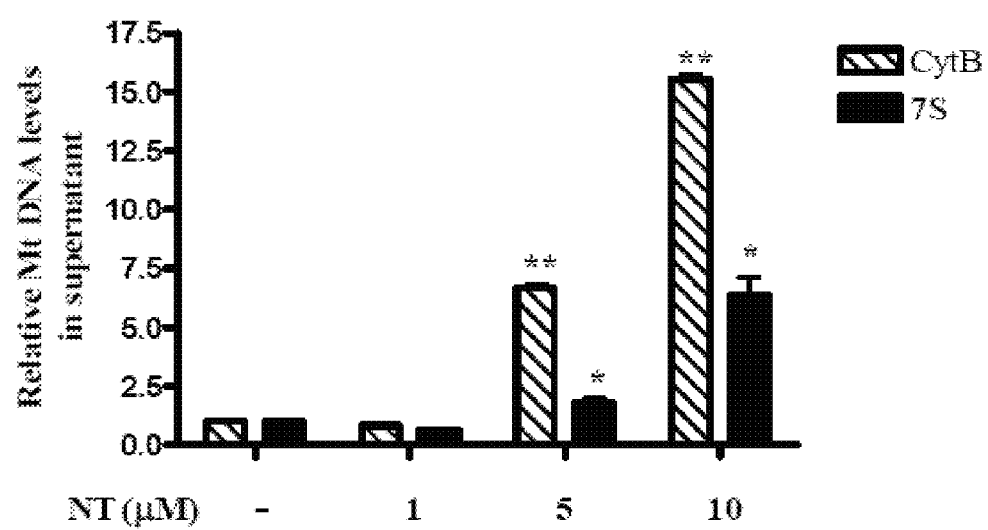
FIG. 9 is a graphic representation of data showing that neurotensin stimulates human mast cells to release mitochondrial DNA.

It has also been surprisingly discovered that neurotensin can stimulate human mast cells to release mitochondrial DNA (FIG. 8A). This disclosure provides a method for inhibiting release of mtDNA by administering to a subject an effective amount of luteolin (FIG. 8B). To assess the inhibition, levels of mtDNA or circulating basophils in the blood are measured. Then, after the administration of neurotensin, measure the levels of mtDNA or basophils again. Alternatively, the levels can be measured in tissue samples.

Methods of Treating

A composition of this disclosure is useful to treat an ASD by inhibiting brain blood vessel leakage. When administered to a subject with an ASD, the disclosed compositions, or therapeutic formulations containing such compositions, modulate at least one behavioral symptom of the disorder being treated. A physician with training in the diagnosis and treatment of the relevant ASD disorder will be able to detect the modulation in the at least one symptom of the relevant disorder. One of the screening tests for such improvement is the Aberrant Behavior Checklist (ABC).

This disclosure is also directed to kits to screen for an ASD in a subject. A kit comprises at least a rapid way of obtaining a blood sample and screening for increased levels of NT, IL-6, IL-9, or MtDNA in the subject. The container can be sterile, permitting a sufficient amount of blood to be drawn into a physiologically acceptable vehicle for immediate or further analysis. The kit can also include a label or instructions to screen for an ASD in a subject.

Although not bound by any particular mechanism of action of the components of the claimed compositions, the inventor contemplates that they inhibit brain blood vessel leakage.

Methods of Screening

This application is also directed to methods of screening a subject to determine whether the subject has an ASD. The method comprises collecting blood from a subject suspected of having an ASD. Next, the serum or plasma is separated from the sample is assayed for the level of a certain biomarker or biomarkers. The expression and/or production of the biomarkers can also be identified in peripheral blood leukocytes from the blood plasma either before or after stimulation with such triggers as phytohemasgglutinin (HPA) or NT in vitro. The biomarker or biomarkers can be, for example, genomic DNA, mitochondrial DNA, IL 6, IL 8, IL 9, IL 13, IL 17, IL 33, prostaglandin D2, corticotrophin releasing hormone, brain derived neuroptrophic factor, heparin sulfate, neurotensin, thymus stromal lymphopoietin, vascular endothelial growth factor, vasoactive intestinal peptide, platelet activating factor, AMA-M2 antibodies, and tryptase. Finally, the level of the biomarker or biomarkers are compared against the level from a subject known not to have an ASD. A higher level of the biomarker in a subject suspected of having an ASD indicates that the subject may have an ASD.

The levels of the biomarkers can be measured by various assays. For example, the levels of neurotensin and IL-6 can be measured by commercially available ELISA kits (e.g. R & D Systems, Indianapolis, Ind.) or by multiplex microbead arrays (e.g., Millipore, Billerica, Mass.). Other methods include intradermal blood sampling and electrochemical detection of some of the biomarkers.

Formulation

This disclosure is also directed to a pharmaceutical formulation comprising at least one disclosed composition, and a pharmaceutically-acceptable carrier. Such formulations are suitable for administration to a subject. The pharmaceutical formulation can be used for treating a disorder described above.

Any suitable pharmaceutically acceptable carrier known in the art can be used as long as it does not affect the inhibitory activity of a disclosed composition. Carriers may be used that efficiently solubilize the agents. Carriers include, but are not limited to, a solid, liquid, or a mixture of a solid and a liquid. The carriers can take the form of capsules, tablets, pills, powders, lozenges, suspensions, emulsions, or syrups. The carriers can include substances that act as flavoring agents, lubricants, solubilizers, suspending agents, binders, stabilizers, tablet disintegrating agents, and encapsulating materials. Other examples of suitable physiologically acceptable carriers are described in *Remington's Pharmaceutical Sciences* (21st ed. 2005), incorporated into this disclosure by reference.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations can conveniently be presented in unit dosage form and can be prepared by any methods known in the art of pharmacy. The amount of a disclosed composition that can be combined with a carrier material to produce a single-dosage form will vary depending upon the subject being treated, the particular mode of administration, the particular condition being treated, and other considerations. The amount of a disclosed composition that can be combined with a carrier material to produce a single-dosage form will generally be that amount of the composition that produces a therapeutic effect. Generally, out of one hundred percent, this amount will range from about 1 percent to about ninety-nine percent of active ingredient, in some instances from about 5 percent to about 70 percent, in other instances from about 10 percent to about 50 percent.

Methods of preparing these formulations or compositions include the step of bringing into association a composition disclosed in this application with a carrier and, optionally, one or more accessory ingredients. In general, the formulations are prepared by uniformly and intimately bringing into association a composition of this disclosure with liquid carriers, or timely divided solid carriers, or both, and then, if necessary, shaping the product.

In solid dosage forms of the disclosed compositions for oral administration (e.g., capsules, tablets, pills, dragees, powders, granules, and the like), the active ingredient is mixed with one or more additional ingredients, such as sodium citrate or dicalcium phosphate, and/or any of the following: (1) fillers or extenders, such as, but not limited to, starches, lactose, sucrose, glucose, mannitol, and/or silicic acid; (2) binders, such as, but not limited to, carboxymethylcellulose, alginates, gelatin, polyvinyl pyrrolidone, sucrose, and/or acacia; (3) humectants, such as, but not limited to, glycerol; (4) disintegrating agents, such as, but not limited to, agar, calcium carbonate, potato or tapioca starch, alginic acid, certain silicates, and sodium carbonate; (5) solution retarding agents, such as, but not limited to, paraffin; (6) absorption accelerators, such as, but not limited to, quaternary ammonium compounds; (7) wetting agents, such as, but not limited to, cetyl alcohol and glycerol monostearate; (8) absorbents, such as, but not limited to, kaolin and bentonite clay; (9) lubricants, such as, but not limited to, talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a composition of this disclosure, excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration can include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet can be made by compression or molding, optionally with one or more accessory ingredients.

In solutions, suspensions, emulsions or syrups, an effective amount of a disclosed composition is dissolved or suspended in a carrier, such as sterile water or an organic solvent, such as aqueous propylene glycol. Other formulations can be made by dispersing the agent in an aqueous starch or sodium carboxymethyl cellulose solution or a suitable oil known to the art. The liquid dosage forms can contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral formulations can also include adjuvants, such as wetting agents, emulsifying and suspending agents, sweetening, flavoring, coloring, perfuming, and preservative agents.

Suspensions can contain, in addition to the disclosed composition, suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration can be presented as a suppository, which can be prepared by mixing one or more compositions of this disclosure with one or more suitable non-irritating excipients or carriers comprising, for example, cocoa butter, polyethylene glycol, a suppository wax or a salicylate, and which is solid at room temperature but liquid at body temperature and, thus, will melt in the rectum or vaginal cavity and release the agents. Formulations suitable for vaginal administration also include, but are not limited to, pessaries, tampons, creams, gels, pastes, foams, or spray formulations containing such carriers as are known in the art to be appropriate.

Dosage forms for the topical or transdermal administration of a composition of this disclosure include, but are not limited to, powders, sprays, ointments, pastes, creams, lotions, gels, solutions, patches, and inhalants. The disclosed composition can be mixed under sterile conditions with a pharmaceutically-acceptable carrier, and with any preservatives, buffers, or propellants.

Ointments, pastes, creams, and gels can contain, in addition to a disclosed composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a composition of this disclosure to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the subject composition in a polymer matrix or gel.

The compositions of this application are administered in a therapeutically effective amount to a patient in need of such treatment. This amount can vary, depending on the activity of the agent utilized, the nature of the disorder, and the health of the patient, among other considerations. A skilled practitioner will appreciate that the therapeutically effective amount of a disclosed composition can be lowered or increased by fine-tuning and/or by administering more than one disclosed composition, or by administering a composition of this disclosure together with a second agent (e.g., antibiotics, antifungals, antivirals, NSAIDS, DMARDS, steroids, etc.). Therapeutically effective amounts can be easily determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., Diabetes, (1993) 42:1179). As is known to those in the art, the effective amount will depend on bioavailability, bioactivity, and biodegradability of the composition of this application.

The concentration range of the flavonoids of the oral formulations can be 10-3,000 mg per tablet or capsule. Generally, where present, the amounts of the unrefined olive kernel extract is about 30-50% of the other active ingredients and can be 300-1200 mg. The number of capsules or tablets to be taken per day is determined by the nature and severity of the medical condition, and is readily determinable by the patient's health provider. Other representative formulations are described in the examples below.

The therapeutically effective amount will vary with the subject being treated. Administration of the composition of this disclosure can be hourly, daily, weekly, monthly, yearly, or a single event. For example, the effective amount of the composition can comprise from about 20 mg/kg body weight to about 500 mg/kg body weight and the tablets or capsules can be administered as 2-4/20 kg body weight. When one or more compositions or agents are combined with a carrier, they can be present in an amount of about 1 weight percent to about 99 weight percent, the remainder being composed of the pharmaceutically-acceptable carrier.

Administration

Methods of administration of the therapeutic formulations comprising the compositions of this disclosure can be by any of a number of methods known in the art. These methods include, but are not limited to, local or systemic administration. Exemplary routes of administration include, but are not limited to, oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce pharmaceutical compositions of the disclosed compositions into the central nervous system by any suitable route, including intraventricular and intrathecal injection. Intraventricular injection can be facilitated by an intraventricular catheter, for example, attached to a reservoir, such as an Ommaya reservoir. Methods of introduction can be provided by rechargeable or biodegradable devices, e.g., depots.

Administration can occur by coating a device, implant, stent, or prosthetic. The compositions of this application can also be used to coat catheters in any situation where catheters are inserted in the body. The compositions of this disclosure may also be used as coatings on implanted medical devices. The coated devices can be used to deliver the disclosed compositions to a subject and to treat or protect against inflammation caused by the device itself. Such medical devices include artificial skins (scaffolding such as naturally occurring polymers, e.g., collagen; man-made polymers, e.g., PTFE, Dacron, PET or polyethylene; self-degrading man-made polymers, e.g., PLA or PGA; biopolymer matrices from animal tissues including fetal and neonatal tissues to be used as tissue engineering scaffolds (cf. Bell et al., U.S. Pat. No. 6,696,074)), artificial joints, band-aids, stents for blood vessels, artificial blood vessels, pacemakers, stents for abdominal support in hernia repair, tissue transplants, prostheses, breast implants, etc. Particularly useful in this regard are compositions containing olive kernel extract in soft gel capsules or other appropriate vehicles.

The therapeutic formulations containing a disclosed composition can also be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compositions can be administered either in the same formulation or in a separate formulation, either simultaneously or sequentially. Thus, an individual who receives such treatment can have a combined (conjoint) effect of different therapeutic compositions.

Other therapeutic agents useful potentially useful in ASDs include antioxidants. Antioxidants can be natural or synthetic. Antioxidants are, for example, superoxide dismutase (SOD), 21-aminosteroids/aminochromans, glutathione, S-adenosyl methionine, vitamin C or vitamin E. Many other antioxidants are known to those of skill in the art. The compositions of this application can serve as part of a treatment regimen that may combine many different anti-inflammatory agents. For example, the subject compositions can be administered in combination with one or more of an NSAID, DMARD, or immunosuppressant.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Example 1

Increased Serum Biomarkers in Autism

Figure 2:
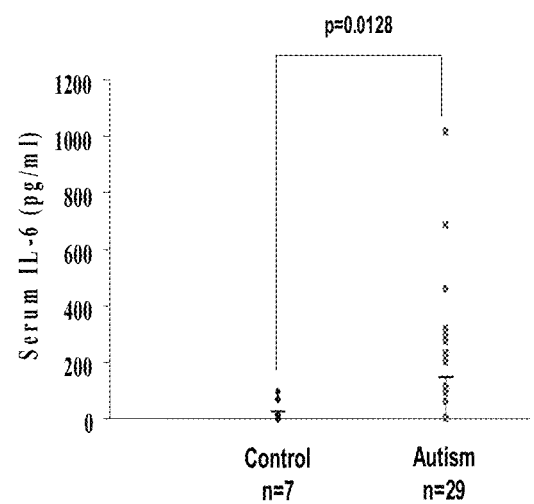
FIG. 2 is a graphic representation of data showing serum levels of interleukin-6 (IL-6) of individual patients (2-4 years old with autism) and age-matched normally developing control patients. That data indicate that there is a statistically significant IL-6 increase in children with autism.

Serum was collected from white, non-Latino healthy subjects (n=7, age: 2.5-4 years old) and children with autism (n=29, age: 2.5-3.5 years old) and analyzed for the following peptides: β-endorphin, NT, and substance P (SP), as well as the following cytokines: IL-1α, IL-1β, IL-4, IL-6, IL-8, IL-10, IL-13, using multiplex microbead arrays (Millipore, Mass.). As shown in FIGS. 1 and 2, only NT and IL-6 showed a statistically significant increase in children with autism as compared to normally developing controls. Thus, both of these molecules could serve as diagnostic biomarkers for ASDs.

Example 2

Inhibitory Effect of Flavonoids on Brain Blood Vessel Leakage

Male BALB/6 mice (6 weeks old, Jackson Laboratories, Bar Harbor, Me.) were injected in their tail vein with 0.2 ml of Evans blue (0.4%). Binding of Evans blue to the albumin found in the blood prevents Evans blue from escaping the circulation and constitutes a good biomarker from extravasation in brain parenchyma.

Figure 3:
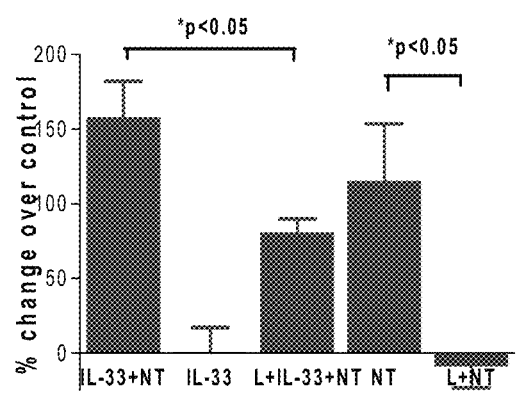
FIG. 3 is a graphic representation of data that shows that intraperitoneal injection of interleukin-33 (IL-33) together with NT induced a statistically significant synergistic increase in brain blood vessel leakage in mice, while pretreatment with intraperitoneal injection of luteolin 10 min prior to injection of IL-33 plus NT inhibited brain blood vessel leakage.

Brain blood vessel leakage was assessed with Evans blue extravasation at 2 hr following Evans blue and 30 min after intraperitoneal injection of NT. Mice were anesthetized with a single intraperitoneal injection of ketamine/xylazine (10 mg/kg and 80 mg/kg body weight, each), an intracardiac catheter was inserted in the left ventricle, blood was withdrawn, and 10 ml normal saline was administered intracardially to wash any Evans blue from the systemic circulation. The mice were then decapitated and the whole brain was removed. For brain extravasated Evans blue measurements, the brains were first weighed and the Evans blue was then extracted in 1 ml of N,N-dimethylformamide overnight at 55° C. and the optical density was measured at 620 nm using a PerkinElmer Luminescence Spectrophotometer (Perkin Elmer, Norwalk, Conn.). EB concentration was calculated using a standard curve and values were normalized to the tissue weight and expressed as arbitrary units/mg of tissue. Five animals per group were estimated to be sufficient for significant differences given the variability (<50%) observed. Results of Evans blue/mg tissue were expressed as mean±SD of percent change from control. This statistical analysis was chosen because it permits the experimental results to be compared to their own control and avoids variability from experiment to experiment. Values were then compared using the non-parametric Mann-Whitney U test. Significance is denoted by $p<0.05$. In order to induce brain blood vessel leakage, the mice were either treated only with an intraperitoneal injection (0.5 ml) of NT (500 nmol/kg body weight) or first pretreated with the flavonoid luteolin (40 mg/kg body weight) mixed in olive kernel extract to permit solubilization and increased absorption of the lipid-soluble luteolin. The mice not treated with luteolin were pretreated the same way only with the vehicle in order to keep the conditions similar [olive kernel extract, obtained from Minerva Edible Oils, Athens, Greece (http://www.minerva.com.gr/)]. As shown in FIG. 3, NT induced 150% increase in brain blood vessel leakage, while pretreatment with luteolin completely inhibited brain blood vessel leakage. When the mice were treated with both IL-33 (1 microg/mouse) and NT, brain leakage was even greater (FIG. 3); IL-33 alone had no effect. Pretreatment with the same amount of luteolin as before inhibited brain blood vessel leakage by 50% (FIG. 3). Using more luteolin could inhibit the synergistic effect of IL-33 and NT.

Example 3

NeuroProtek®

NeuroProtek® contains (Table 1) the quercetin glycoside rutin that gets cleaved by intestinal bacteria and acts primarily on the gut. Quercetin is metabolized as "decoy" and allows higher absorption of the lipophilic flavone luteolin. Increased absorption of luteolin is further achieved by formulation in olive kernel extract that forms liposomes that increase absorption.

Quercetin at 10 μM was sufficient to inhibit mast cells by 80%. The amount of 10 μM is 10 mg per 1 liter=1 kg, or 200 mg per 20 kg body weight, assuming that the body is one compartment with equal distribution and complete absorption. Thus, assuming maximal 30% absorption of the flavonoids, then administration is 3×200=600 mg/20 kg body weight. Each NeuroProtek® capsule contains a total of 300 mg flavonoids (Table 1). Thus, two capsules will deliver the required 600 mg/20 kg body weight.

The specific flavonoids proposed are safe. (Harwood M, Danielewska-Nikiel B, Borzelleca J F, Flamm G W, Williams G M, Lines T C. A critical review of the data related to the safety of quercetin and lack of evidence of in vivo toxicity, including lack of genotoxic/carcinogenic properties. *Food Chem Toxicol.* 2007 November; 45(11):2179-205).

Preferred sources of the select flavonoids can be from Pharma Science Nutrients, Inc., Ocala, Fla., while this formulation can be made by GMP-Certified Tishcon Corp., Salisbury, Md.).

TABLE 1

The composition of NeuroProtek®

| Ingredient | Chemical entity | Source | Purity | Amount (mg/dose) |
|---|---|---|---|---|
| Luteolin | Flavone | Chamomile | 97% | 30 |
| Quercetin | Flavonol | Chamomile | 99% | 170 |
| Rutin | Flavonoid glycoside | Saphora plant | 99% | 100 |
| Olive kernel extract | Oil | Olive seeds | 99% | 40% weight/weight |

Example 4

Effectiveness of NeuroProtek® on Children with Autism

Diagnosis of the specific subjects was made using the Autism Diagnostic Observation Schedule-Generic (ADOS-G, a patient observational tool); follow-up was performed with the ABC screening test. The first subject was an 8 year old boy with Autism and a rash that had never been diagnosed. He had diarrhea when his skin flared up. He had been to allergists and dermatologists for years; they believed he is not allergic. The child was given 2 capsules of NeuroProtek®/20 kg body weight per day. Six months later his behavior improved significantly in that he was as easily excitable and did not purposely repeat arm gestures as before. He was more patient and managed to put letter blocks together to form words.

Patient A: A 5 Year Old Girl with Atypical Autism (PDD-NOS)

The girl would not allow the health provider to come near her. She would hide under the table and scream if addressed more than once. She was put on 2 capsules of NeuroProtek®/20 kg body weight per day. Six months later, her ability to interact with others and learn simple words improved significantly. She would allow the health provider to hold her and help her make simple drawings.

Patient B: A Three Year Old Girl with Autism

The girl had not spoken or interacted with anyone since her diagnosis one year ago. She was administered NeuroProtek® starting on Oct. 13, 2010. On Dec. 3, 2010, she spoke for the first time. On Dec. 22, 2010, she came into the office and started talking, singing and asked if she could draw. Teachers observed significant changes in the girl. The girl started interacting with other students on a regular basis and now goes out into the recess area to play with other students.

Patient C: A 10 Year-Old Boy with Autism

The boy is deep in the autistic spectrum and could not speak or write. After being on NeuroProtek® for over one month, he drew a card for the first time. He has been on NeuroProtek® since Oct. 18, 2010. In November, he began communicating and understanding his brothers much clearer. By the beginning of December, his teacher observed improvement in his focus and comprehension. His test scores and homework showed significant improvement. The boy is the only special needs child in the troop and the leader observed that he was the only one to finish a project and he was the only one to understand the directions and not ask for assistance doing it. The troop leader noted that his focus, understanding, and social skills have changed drastically within the last couple of weeks.

Patient D: A 4 Year Old Girl with Autism

The girl been one taking NeuroProtek® for one month. Health care providers observed that her feces was no longer typical autism spectrum feces, but solid, clean and not difficult for her. They also noticed an improvement in her focus and speech. Her family observed that was noticeably more social. The girl has also hugged a neighbor and hugged her mother and father without prompting.

Example 5

Inhibition of Mast Cell Activation $HgCl_2$ was obtained from Fluka Chemical Corp. (Milwaukee, Wis.). Thimerosal, sodium salicylate, methyl thiosalicylate, Substance P (SP), ibuprofen and luteolin were obtained from Sigma-Aldrich (St. Louis, Mo.). $HgCl_2$ was dissolved in Dulbecco's phosphate buffered saline (DPBS, GIBCO, Grand Island, N.Y.). Luteolin was dissolved in dimethylsulfoxide (DMSO), but the final concentration was less than 0.1%. Other drugs were dissolved in distilled water the day of the experiments.

Human Cultured Mast Cells

LAD2 human mast cells were cultured in serum-free media (StemPro-34; GIBCO, Grand Island, N.Y.) supplemented with 2 mM L-glutamine, 100 IU/ml penicillin, 50 µg/ml streptomycin, and 100 ng/ml recombinant human Stem Cell Factor (rhSCF, obtained from Amgen, Inc., Thousand Oaks, Calif.). For optimal cell growth, LAD2 cell density was maintained between $0.5 \times 10^6$ and $1 \times 10^6$ cells/ml. Cell viability was assessed at 1 and 24 hr using trypan blue (0.3%) exclusion.

VEGF Assay

LAD2 cells were washed with DPBS and suspended in complete culture medium. LAD2 cells ($2 \times 10^5$ cells/well/200 µl) were plated in 96 well flat bottom Falcon cell culture plates (Becton Dickinson, Franklin Lakes, N.J.) and were pre-incubated for 15 min at 37° C. in 5% $CO_2$ atmosphere. The cells were then incubated with either SP (2 µM), $HgCl_2$ (10 µM), or thimerosal (1, 10 µM) for 24 hours at 37° C. Control cells were treated with equal volume of only culture medium. For the inhibition experiments, thimerosal or methyl thiosalicylate were added together with the triggers, while luteolin was added 10 min before the triggers. After the reaction time, plates were centrifuged and the supernatant was gently collected from the wells and stored at −20° C. until VEGF was measured by Enzyme-Linked Immunosorbent Assay (ELISA) using a commercial kit (R&D Systems, Minneapolis, Minn.). The minimum detectable level of VEGF was 5 pg/ml.

Effect of Thimerosal on Mast Cells Viability

Figure 4A:
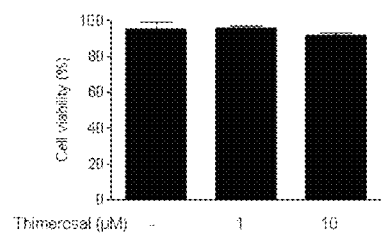
FIG. 4A is a graphic representation of data for the viability of LAD2 mast cells incubated with thimerosal for 24 hours in the culture medium

LAD2 mast cells were incubated with thimerosal for 24 hours in the culture medium and their viability was assessed by trypan blue exclusion. Viability was decreased by less than 10% only at thimerosal concentrations of 10 µM (FIG. 4A).

Effect of Thimerosal on LAD2 Mast Cell VEGF Release

Figure 4B:
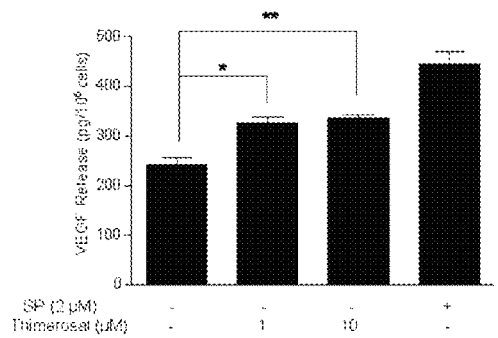
FIG. 4B is graphic representation of data showing the effect of thimerosal on LAD2 mast cell VEGF release.

LAD2 cells stimulated with thimerosal for 24 hours released significantly more VEGF at 1 and 10 µM ($326 \pm 12$ pg/$10^6$ cells, $335 \pm 12$ pg/$10^6$ cells), respectively compared to control ($242.5 \pm 21$ pg/$10^6$ cells) (n=5, $p<0.05$, FIG. 4B).

Figure 5A:
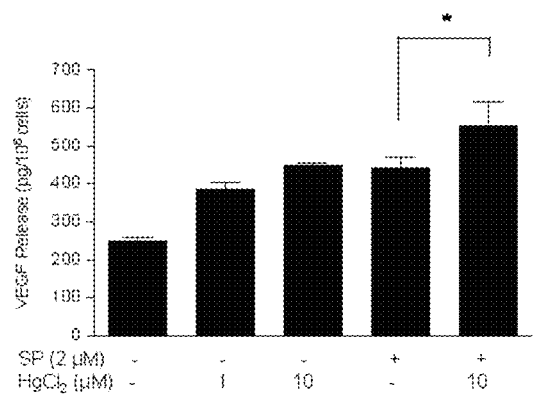
FIG. 5A is a graphic representation of data showing the effect of HgCl$_2$ on SP-induced VEGF release.
Figure 5B:
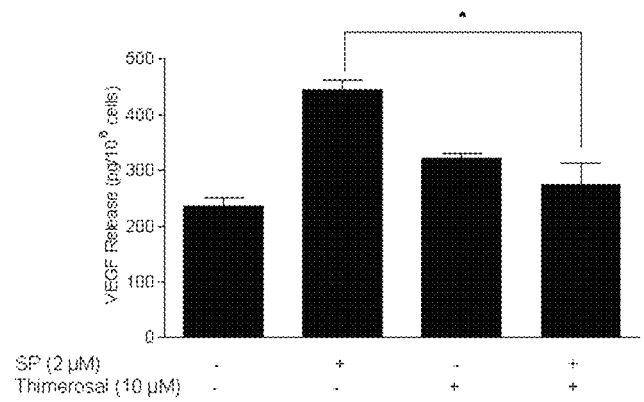
FIG. 5B is a graphic representation of data showing the effect of thimerosal SP-induced VEGF release.

Effect of Thimerosal on SP-Induced VEGF Release $HgCl_2$ (10 µM) added together with SP (2 µM) had a statistically significant effect in augmenting VEGF release ($553 \pm 63$ pg/$10^6$ cells) as compared to SP alone ($445 \pm 16$ pg/$10^6$ cells) (FIG. 5A). In contrast, thimerosal (10 µM) added together with SP (2 µM) inhibited SP-induced VEGF release to $274.5 \pm 35$ pg/$10^6$ cells (n=3, $p<0.05$, FIG. 5B). There was no statistical difference between thimerosal alone and thimerosal with SP.

Effect of Methyl Thiosalicylate on $HgCl_2$ and SP-Induced VEGF Release

Figure 6A:
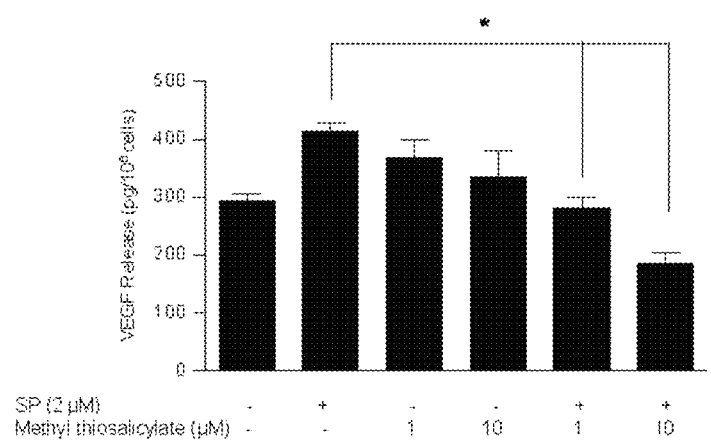
FIG. 6A is a graphic representation of data showing the effect of methyl thiosalicylate on SP-induced VEGF release.
Figure 6B:
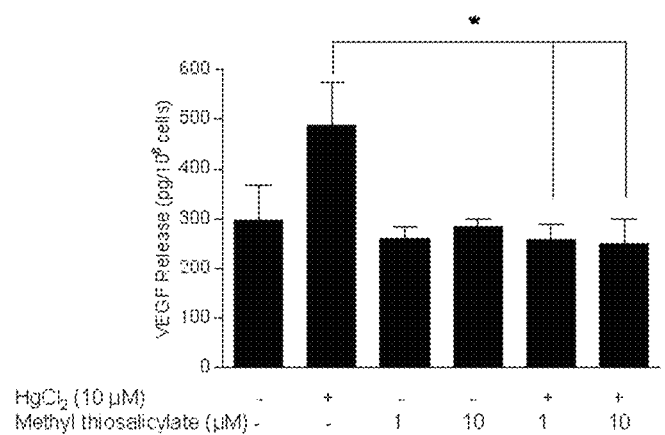
FIG. 6B is a graphic representation of data showing the effect of methyl thiosalicylate on HgCl$_2$-induced VEGF release.

In view of the fact that thimerosal inhibited the effect of SP, the inhibition was due to its thiosalicylate component. Thus, the effect of methyl thiosalicylate on SP-induced VEGF release was examined. Methyl thiosalicylate (1, 10 µM) added with the trigger inhibited SP (2 µM)-induced VEGF release from $413.72 \pm 18$ pg/$10^6$ cells to $281.63 \pm 24$ pg/$10^6$ cells at 1 µM and $185.85 \pm 23$ pg/$10^6$ cells at 10 µM (FIG. 6A). Methyl thiosalicylate (1, 10 µM) also inhibited $HgCl_2$ (10 µM)-induced VEGF release from $488 \pm 76$ pg/$10^6$ cells to $258 \pm 29$ and $249.5 \pm 24$ pg/$10^6$ cells, respectively (n=3, $p<0.05$, FIG. 6B).

Effect of Luteolin on Thimerosal and HgCl2-Induced VEGF Release

Figure 7:
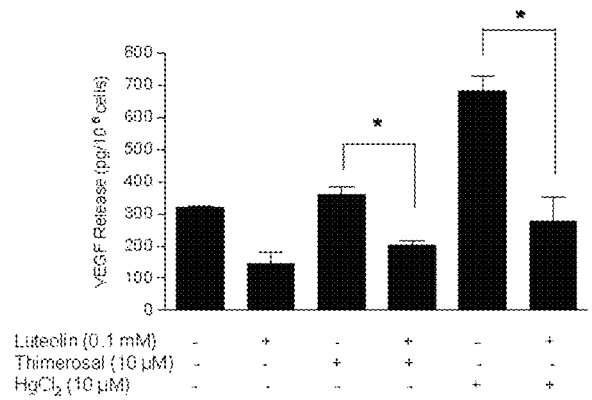
FIG. 7 is a graphic representation of data showing the effect of luteolin on thimerosal and HgCl$_2$-induced VEGF release.

Luteolin is a flavonoid that inhibits mast cell secretion. Thus, whether luteolin could inhibit thimerosal or $HgCl_2$-induced VEGF release was investigated. Pretreatment (10 min) of LAD2 cells with luteolin (0.1 mM) blocked VEGF release (100% inhibition) stimulated by either thimerosal (10 µM) or HgCl2 (10 µM) (n=3, $p<0.05$, FIG. 7).

Example 6

Mitochondrial DNA

A homogeneous group of young Caucasian children with the same endophenotype was investigated. Subjects were diagnosed with autistic disorder using the ADI-R and ADOS-G scales, which have been validated in the Greek population. There were no apparent clinical differences, such as gastrointestinal problems, as reported by the parents, or mitochondrial dysfunction, as indirectly suggested by normal plasma lactate/pyruvate ratio, that may have allowed separation of the autistic patients in subgroups.

Blood was obtained in the morning at least 2 hours after breakfast to minimize any diurnal or postprandial effects. Serum from patients and controls was aliquoted and frozen at −80° C. until assayed. All samples were labeled only with a code number, as well as the age and sex of the respective subject. Patients were selected from the Second Department of Psychiatry at Attikon General Hospital, University of Athens Medical School (Athens, Greece), and an NIH-approved site for biological samples. Parents signed an appropriate consent form according to the Helsinki Principles. All children met ICD-10 criteria for autistic disorder. The exclusion criteria included: (1) any medical condition likely to be etiological for ASD (e.g. Rett syndrome, focal epilepsy, fragile X syndrome or tuberous sclerosis); (2) any neurologic disorder involving pathology above the brain stem, other than uncomplicated non-focal epilepsy; (3) contemporaneous evidence, or unequivocal retrospective evidence, of probable neonatal brain damage; (4) any genetic syndrome involving the CNS, even if the link with autism is uncertain; (5) clinically significant visual or auditory impairment, even after correction; (6) any circumstances that might possibly account for the picture of autism (e.g. severe nutritional or psychological deprivation); (7) active treatment with pharmacological or other agents; (8) mastocytosis (including urticaria pigmentosa); (9) history of upper airway diseases; (10) history of inflammatory diseases; and (11) history of allergies. The controls were normally developing, healthy children, unrelated to the autistic subjects, and were seen for routine health visits at the Pediatric Department of the Institute of Social Health Insurance, Thessaloniki, Greece. There were no identifiers except for age and sex. All autistic and control samples were collected over a period of six month by trained health providers. Serum was prepared immediately and stored in −80° C. All autism and control samples were then transported by the senior author on dry ice to Boston for analysis. Previous work has shown that samples are stable at this temperature. Moreover, DNA is known to be fairly stable and can be stored for months even at −20° C.

Anti-mt antibody Type 2 (AMA-M2) was detected using a commercial EIA Kit (DRG International, Germany). Total DNA was extracted from serum samples using Qiagen DNA Micro extraction kit (Qiagen, Calif.). Mitochondrial specific DNA for Cytochrome B (mt-CytB) and 7S (mt-7S) was detected and quantified by Real time PCR using Taqman assay (Mt-7S: Hs02596861_s1; Mt-CYB: Hs02596867_s1; GAPDH: Hu, VIC, TAMRA, Applied Biosystems, Calif.). GAPDH DNA was used to exclude any genomic "contamination." Total DNA was isolated from supernatant fluids of cultured LAD2 cells using the same method.

Culture of LAD2 Mast Cells

LAD2 cells (NIH, Bethesda, Md., USA) were cultured in StemPro-34 SFM Medium (Invitrogen, Carlsbad, Calif.) supplemented with 100 ng/ml recombinant human stem cell factor (rhSCF, from Biovitrum, Sweden) and 1% U/ml penicillin/streptomycin. Cells were grown in an incubator in 5% CO2 and air environment at 37° C. All cells were used during their logarithmic growth period.

Statistical Analysis

Samples were thawed. The results are presented as scattergrams, with the horizontal lines indicating the means. The ASD group was compared to the control using unpaired, unequal, 2-tailed, Student's t-test, as well as the non-parametric Mann-Whitney U test. Any correlation between independent variables (mt-CytB DNA and mt-7S DNA, as well as mt-CytB DNA and AMA-M2 protein amount) was investigated using linear regression analysis. Significance of comparisons between healthy subjects and subjects with ASD is denoted by $p<0.05$.

Results

Serum samples from autistic patients were tested for mtDNA (n=20; 16 males and 4 females; mean age 3.0±0.4 years) and AMA-M2 antibodies (n=14; 11 males and 3 females; mean age 3.0±0.4 years) compared to controls (n=12; 11 males and 1 female; mean age 3±1.2 years).

The serum from young autistic children contains significantly higher amounts of mt-CytB (p=0.0002) and for mt-7S (p=0.006) (FIGS. 8A and 8B). Linear regression shows an excellent correlation ($R^2$=0.89) between mt-CytB and 7S. No presence of GAPDH DNA was detected indicating there was no genomic DNA release.

Figure 10:
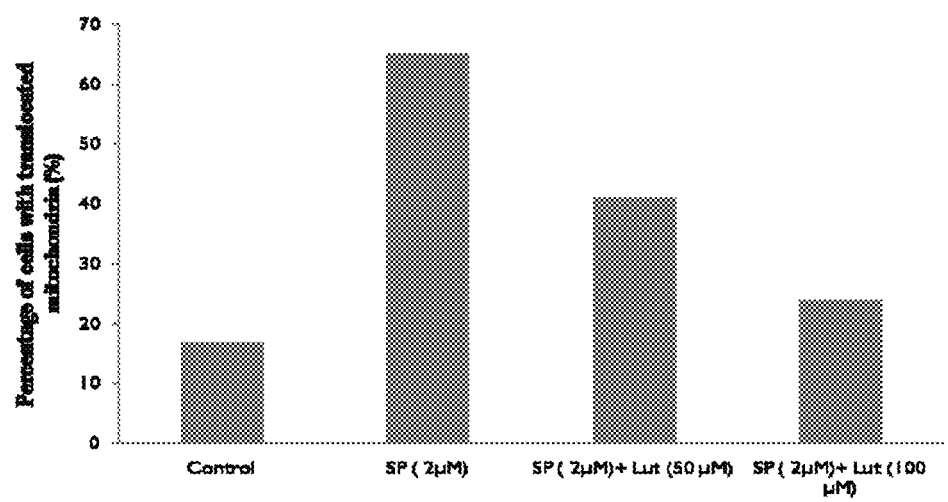
FIG. 10 is a graphic representation of data showing the inhibition by luteolin of neurotensin-induced release of mitochondrial DNA from human mast cells.

NT is also able to trigger release of extracellular mt components from human mast cells. Stimulation of human cultured LAD2 cells with NT (1, 5 and 10 micro M, for 1 h at 37° C.) resulted in significant release of CytB and 7S mtDNA in the supernatant fluid (FIG. 10).

As before for neurotensin, cultured mass cells were pretreated for 5 min with luteolin. The release of extracellular mt components from mast cells can be inhibited by luteolin (FIG. 11).

Mitochondrial DNA Assay

Total DNA was extracted from supernatant fluids of cultured LAD2 cells using Qiagen DNA Micro extraction kit (Qiagen, Calif.). Mitochondrial specific DNA for Cytochrome B (Mt-CytB) and 7S (Mt-7S) was detected and quantified by Real time PCR using Taqman assay (Mt-7S: Hs02596861_s1; Mt-CYB: Hs02596867_s1; GAPDH: Hu, VIC, TAMRA, Applied Biosystems, Calif.). GAPDH DNA was used to exclude any genomic "contamination."

Statistical Analysis

All conditions were performed in triplicate, and all experiments were repeated up to five times (n=3-5). Results are presented as mean±SD. Data from two conditions, such as between stimulated and control samples, were compared using the unpaired 2-tailed, Student's t-test. Significance of comparisons is denoted by $p<0.05$.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:

1. A method of treating an autism spectrum disorder, comprising administering to a subject in need thereof an effective amount of a composition comprising flavonoids and olive kernel extract, wherein the flavonoids are present in an amount of 10-3,000 mg per tablet or capsule and comprise luteolin, quercetin, and rutin, and optionally, a serotonin receptor antagonist, a defensin, a histamine-1 receptor antagonist, a histamine-3 receptor agonist, or an antipsychotic agent, wherein the composition inhibits brain blood vessel leakage.

2. The method of claim 1, wherein the autism spectrum disorder is selected from the group consisting of Autism, Asperger's syndrome, atypical autism otherwise known as pervasive developmental disorder not otherwise specified (PDD-NOS), Rett syndrome, childhood disintegrative disorder, and sensory integration dysfunction.

3. The method of claim 1, wherein the autism spectrum disorder is autism.

4. The method of claim 1, wherein the autism spectrum disorder is Asperger's disorder.

5. The method of claim 1, wherein the autism spectrum disorder is Rett syndrome.

6. The method of claim 1, wherein the serotonin receptor antagonist is azatadine or cyproheptadine.

7. The method of claim 1, wherein the histamine-1 receptor antagonist is azelastine, azatadine, hydroxyzine, merelastine, or, rupatadine.

8. The method of claim 1, wherein the histamine-3 receptor agonist is R(−)-α-methyl histamine, $N^\alpha$-methyl histamine, $N^\tau$-methyl histamine, α-$N^\alpha$-dethylhistamine, α,β-dimethyl histamine, $N^\alpha$-methyl-α-(dimethyl)histamine, $N^\alpha$-methyl-α-(chloromethyl)histamine, or α,β-difluoro-$N^\alpha$-(fluoromethyl)histamine.

9. The method of claim 1 wherein the antipsychotic agent is risperidone.

10. The method of claim 1 wherein the defensin is peptide LL37.

11. The method of claim 1, wherein the composition is administered by oral or parenteral routes.

* * * * *